US010451629B2

(12) United States Patent
Takinami

(10) Patent No.: US 10,451,629 B2
(45) Date of Patent: Oct. 22, 2019

(54) COMPONENT MEASURING DEVICE

(71) Applicant: TERUMO KABUSHIKI KAISHA, Tokyo (JP)

(72) Inventor: Masao Takinami, Asaka (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 226 days.

(21) Appl. No.: 15/275,938

(22) Filed: Sep. 26, 2016

(65) Prior Publication Data

US 2017/0010273 A1 Jan. 12, 2017

Related U.S. Application Data

(63) Continuation of application No. PCT/JP2015/051326, filed on Jan. 20, 2015.

(30) Foreign Application Priority Data

Mar. 27, 2014 (JP) .................. 2014-065162

(51) Int. Cl.
*G01N 33/66* (2006.01)
*G01N 21/78* (2006.01)
(Continued)

(52) U.S. Cl.
CPC .......... *G01N 33/66* (2013.01); *A61B 5/1455* (2013.01); *A61B 5/14532* (2013.01);
(Continued)

(58) Field of Classification Search
CPC .... G01N 33/66; G01N 21/274; G01N 21/251; G01N 33/80; G01N 33/493; G01N 33/49;
(Continued)

(56) References Cited

U.S. PATENT DOCUMENTS

2005/0256382 A1* 11/2005 Eisenmann ........ G01N 33/4875
600/309
2011/0189062 A1* 8/2011 DeAngeli ........ G01N 33/48757
422/400
2013/0273528 A1* 10/2013 Ehrenkranz ...... G01N 33/54366
435/6.1

FOREIGN PATENT DOCUMENTS

JP    S62-019737    1/1987
JP    H10-505676    6/1998
(Continued)

OTHER PUBLICATIONS

International Search Report (with English machine translation) for International (PCT) Patent Application No. PCT/JP2015/051326, dated Apr. 21, 2015, 5 pages.
(Continued)

*Primary Examiner* — Dennis White
(74) *Attorney, Agent, or Firm* — Jason H. Vick; Sheridan Ross, PC

(57) ABSTRACT

A component measuring device includes a calibration member that is slidably disposed in an insertion hole of a chip attachment unit and a biasing member that biases the calibration member toward an insertion port. The calibration member is held by the biasing member at a position where the calibration member blocks the introduction port and a lead-out port and where light from a light emitter is applied to the calibration member when a measuring chip is not inserted in the insertion hole, and slides to a side opposite to the insertion port along with insertion of the measuring chip into the insertion hole so that light from the light emitter is applied to the measuring chip.

18 Claims, 8 Drawing Sheets

(51) Int. Cl.
*G01N 21/27* (2006.01)
*A61B 5/145* (2006.01)
*G01N 33/49* (2006.01)
*G01N 33/493* (2006.01)
*A61B 5/1455* (2006.01)
*A61B 5/15* (2006.01)
*A61B 5/157* (2006.01)
*G01N 21/25* (2006.01)
*G01N 33/80* (2006.01)
*G01N 21/77* (2006.01)

(52) U.S. Cl.
CPC ........ *A61B 5/157* (2013.01); *A61B 5/150022* (2013.01); *A61B 5/150343* (2013.01); *A61B 5/150358* (2013.01); *G01N 21/251* (2013.01); *G01N 21/274* (2013.01); *G01N 21/276* (2013.01); *G01N 21/78* (2013.01); *G01N 33/49* (2013.01); *G01N 33/493* (2013.01); *G01N 33/80* (2013.01); *G01N 2021/7759* (2013.01); *G01N 2201/062* (2013.01)

(58) Field of Classification Search
CPC ................ G01N 21/276; G01N 21/78; G01N 2201/062; G01N 2021/7759; A61B 5/150343; A61B 5/157; A61B 5/150358; A61B 5/150022; A61B 5/1455; A61B 5/14532

See application file for complete search history.

(56) References Cited

FOREIGN PATENT DOCUMENTS

| JP | H10-505677 | 6/1998 |
|----|------------|--------|
| JP | 2004-233271 | 8/2004 |
| WO | WO 9607893 | 3/1996 |
| WO | WO 9607908 | 3/1996 |
| WO | WO 2010/113564 | 10/2010 |

OTHER PUBLICATIONS

Written Opinion (no translation) for International (PCT) Patent Application No. PCT/JP2015/051326, dated Apr. 21, 2015, 4 pages.
International Preliminary Report on Patentability for International Application No. PCT/JP2015/051326, dated Oct. 6, 2016.

* cited by examiner

COMPONENT MEASURING DEVICE

CROSS REFERENCE TO RELATED APPLICATIONS

This Application is a continuation of and claims priority to PCT Application No. PCT/JP2015/051326, filed Jan. 20, 2015, which claims priority to Japanese Application Number 2014-065162, filed Mar. 27, 2014; both of these applications are incorporated herein by reference in their entirety for all that they teach and for all purposes.

TECHNICAL FIELD

The present invention relates to a component measuring device that measures a predetermined component in a body fluid taken into a measuring chip.

BACKGROUND

Conventionally, there has been widely used a component measuring device that measures a predetermined component in a body fluid such as blood or urine. With this type of component measuring device, there is known a colorimetric component measuring device in which a sample, for example, blood, is adhered to a test pad provided in a strip, and the degree of coloration caused by a reaction between a reagent impregnated in the test pad and the sample is optically measured (e.g., refer to Japanese Patent Application, JP 10-505676 W).

The colorimetric component measuring device is provided with a strip holder which includes a strip path (insertion hole) into which the strip is inserted, a light emitter which applies light to the test pad through a hole open on a wall surface of the strip path, and a light receiver which receives reflected light from the test pad. Further, biasing means for biasing the strip toward the hole is disposed at a position facing the hole, and a gray target (calibration member) is provided in the biasing means.

According to such a configuration, when a predetermined component in a body fluid is measured, it is possible to measure the light reflectivity of the gray target of the biasing means before the strip is inserted into the strip path and adjust (calibrate) the optical energy amount of the light emitter on the basis of the measurement result. Accordingly, it is possible to reduce measurement variations caused by aging of the optical system.

SUMMARY

However, in the above conventional technique, a space for inserting the tip of the strip is formed between the hole and the biasing means when the strip is not inserted in the strip path. Thus, disadvantageously, the light emitter and the light receiver are contaminated with foreign substances intruded from the outside through the strip path. When the light emitter and the light receiver are contaminated, a predetermined component in a body fluid may not be accurately measured.

For example, a cover member which reduces the intrusion of foreign substances into the strip path may be detachably attached to the strip holder to reduce the contamination of the light emitter and the light receiver. However, in this case, an attachment/detachment operation for the cover member is required every time a body fluid component is measured, which takes some time.

The embodiments herein have been made in view of such problems, and an object thereof is to provide a component measuring device that makes it possible to improve the working efficiency, to reduce the contamination of a light emitter and a light receiver, and to accurately measure a predetermined component in a body fluid.

A component measuring device can be a component measuring device that measures a predetermined component in a body fluid taken into a measuring chip, including: a chip attachment unit including an insertion hole into which the measuring chip is insertable; a light emitter that applies light to the measuring chip through an introduction port open on a wall surface constituting the insertion hole; a light receiver that receives light from the measuring chip guided through a lead-out port open on the wall surface constituting the insertion hole; a calibration member disposed in the insertion hole slidably along an insertion direction of the measuring chip; and biasing means for biasing the calibration member toward an insertion port of the insertion hole, wherein the calibration member is held by the biasing means at a position where the calibration member blocks the introduction port and the lead-out port and where light from the light emitter is applied to the calibration member when the measuring chip is not inserted in the insertion hole, and slides to a side opposite to the insertion port along with insertion of the measuring chip into the insertion hole so that light from the light emitter is applied to the measuring chip.

According to embodiments of the component measuring device, the introduction port and the lead-out port are blocked with the calibration member when the measuring chip is not inserted in the insertion hole. Thus, the intrusion of foreign substances into the introduction port and the lead-out port from the outside is reduced without providing a cover member for reducing the intrusion of foreign substances into the insertion hole. Thus, it is possible to improve the working efficiency (an attachment/detachment operation for the cover member is not required) and to reduce the contamination of the light emitter and the light receiver. Further, at this time, the calibration member is held by the biasing means at a position where light from the light emitter is applied to the calibration member. Thus, the component measuring device can be calibrated on the basis of a light receiving signal of the light receiver receiving light from the calibration member. When the measuring chip is inserted into the insertion hole, the calibration member slides, and light from the light emitter is applied to the measuring chip. Thus, it is possible to accurately measure a predetermined component in a body fluid taken into a measuring chip.

The component measuring device may further include a calibration controller that calibrates the component measuring device on the basis of a light receiving signal of the light receiver receiving light from the calibration member and a light receiving signal of the light receiver receiving light from the measuring chip before taking the body fluid.

According to such a configuration, two-point calibration using the calibration member and the measuring chip before taking a body fluid can be performed. Thus, it is possible to appropriately calibrate the component measuring device.

The component measuring device may further include an ejector that slides the calibration member toward the insertion port to detach the measuring chip from the insertion hole.

According to such a configuration, the measuring chip can be easily and reliably detached from the insertion hole. Further, when the measuring chip is detached, it is possible to appropriately reduce the intrusion of foreign substances into the introduction port and the lead-out port from the outside through the insertion hole.

In the component measuring device, the biasing means may be disposed at a side opposite to the insertion port with respect to the calibration member in the insertion hole and may include an insertion path through which the ejector is inserted.

According to such a configuration, the ejector can be guided to the calibration member through the insertion path of the biasing means. Thus, the component measuring device can be downsized.

In the component measuring device, the biasing means may be a compression coil spring including the insertion path on the center thereof.

According to such a configuration, since the biasing means is a compression coil spring, the configuration of the biasing member can be simplified.

In the component measuring device, the introduction port and the lead-out port may face each other, and the light receiver may receive transmitted light from the calibration member or the measuring chip.

According to such a configuration, a predetermined component in a body fluid can be accurately measured by transmission measurement of light.

In the component measuring device, the introduction port and the lead-out port may form one opening, and the light receiver may receive reflected light from the calibration member or the measuring chip.

According to such a configuration, a predetermined component in a body fluid can be accurately measured by reflection measurement of light.

Accordingly to the embodiments, the calibration member can be held by the biasing means at the position where the calibration member blocks the introduction port and the lead-out port and where light from the light emitter is applied to the calibration member when the measuring chip is not inserted in the insertion hole. Thus, it is possible to improve the working efficiency, to reduce the contamination of the light emitter and the light receiver, and to accurately measure a predetermined component in a body fluid.

DETAILED DESCRIPTION

Hereinbelow, embodiments of a component measuring device will be described with reference to the accompanying drawings.

Figure 1:
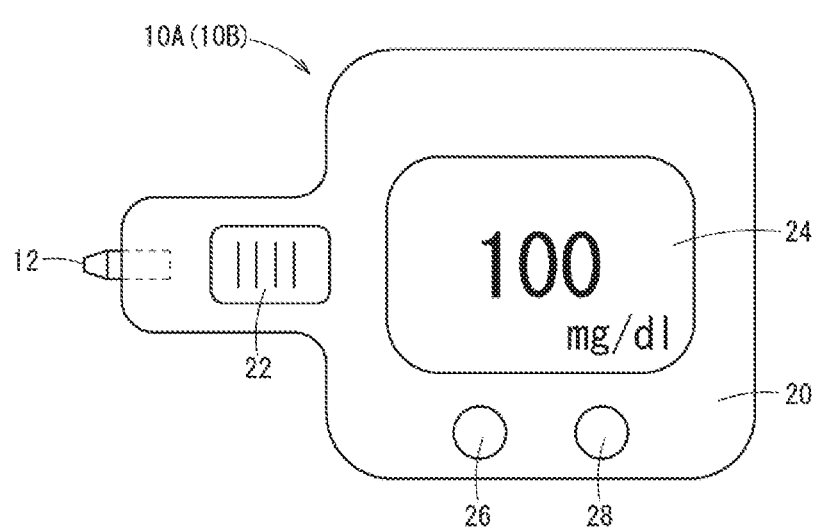
FIG. 1 is a plan view illustrating an embodiment of a blood glucose meter.

As illustrated in FIG. 1, a blood glucose meter 10A, as a component measuring device, is a colorimetric blood glucose meter which is capable of attaching a measuring chip 12, as a test tool, to the tip thereof and optically transmission-measures a glucose concentration (blood glucose level) in blood taken into the measuring chip 12.

The blood glucose meter 10A is mainly for personal use in which a user (patient) operates the blood glucose meter 10A by himself/herself to perform blood glucose measurement. However, it is needless to say that the blood glucose meter 10A can also be used by medical professionals in medical facilities without special modifications.

Figure 2:
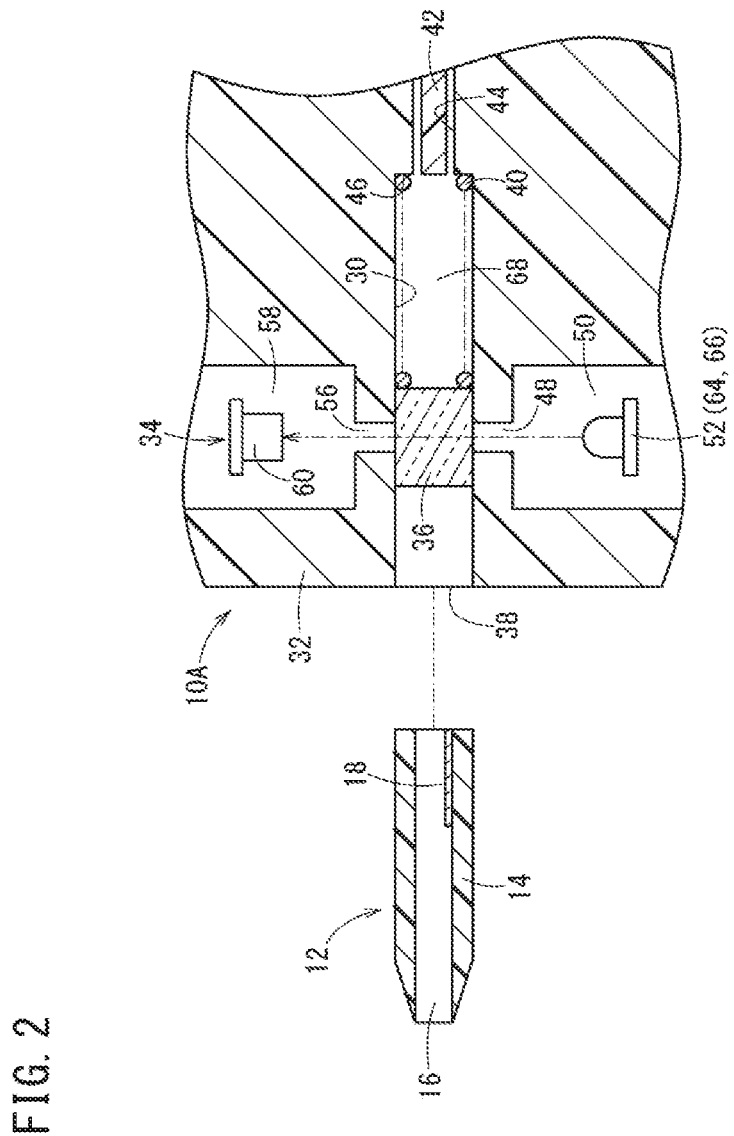
FIG. 2 is a longitudinal sectional view of the blood glucose meter and a measuring chip of FIG. 1.

First, the measuring chip 12 will be described. The measuring chip 12 is a so-called disposable product, packaged individually or together with a certain number of measuring chips 12, and taken out and attached to the blood glucose meter every time measurement is performed. As illustrated in FIG. 2, the measuring chip 12 is provided with a chip body 14. The chip body 14 is preferably formed in a tapered shape having a tapered tip so as to easily perform spot application of blood. Although, the chip body 14 has a quadrangular cross section, the cross section of the chip body 14 may have a circular shape or a polygonal shape (except a quadrangular shape) that produces a capillary phenomenon.

The chip body 14 is made of, for example, a resin material having high transparency such as polymethyl methacrylate, polystyrene, cyclic polyolefin or polycarbonate, glass, or quartz for the application and reception of light. A blood introduction path 16 which is thin enough to suck blood by a capillary phenomenon is formed in the chip body 14. A reagent (coloring reagent) 18, which shows a color corresponding to a blood glucose concentration by a reaction with blood, is applied to a base end side of a wall surface constituting the blood introduction path 16.

Although, the blood introduction path 16 is formed in a quadrangular shape when viewed from an extending direction thereof, the blood introduction path 16 may be formed in a circular shape or a polygonal shape (except a quadrangular shape). In the measuring chip 12 configured in this manner, the chip body 14 may be separable (e.g., equally separable) in a short-side direction. In this case, the reagent 18 can be easily applied to the wall surface constituting the blood introduction path 16.

Next, the blood glucose meter 10A will be described. In the following description, in the blood glucose meter 10A, a side to which the measuring chip 12 is attached is referred to as a "tip side" and a side opposite thereto is referred to as a "base end side". The same applies to a blood glucose meter 10B described below.

As illustrated in FIG. 1, the blood glucose meter 10A includes a casing 20 which constitutes the outer appearance thereof. The tip side of the casing 20 has a narrow width, and the base end side of the casing 20 has a size easily grasped with one hand. An ejection lever 22 for detaching the measuring chip 12 from the blood glucose meter 10A, a display 24 which includes a liquid crystal or an LED, a power button 26 which turns on/off the blood glucose meter 10A, and an operation button 28 are disposed on the upper face of the casing 20.

In embodiments, a user presses the power button 26 to turn on a power source 72 (refer to FIG. 3) of the blood glucose meter 10A to operate the display 24, and a blood glucose measured value is displayed on the display 24. Further, a past blood glucose measured value can be displayed on the display 24 by operating the operation button 28.

As illustrated in FIG. 2, a chip attachment unit 32 which includes an insertion hole 30 into which the measuring chip 12 is insertable, an optical measurement unit 34 for optically measuring a blood glucose level in blood taken into the measuring chip 12, a calibration member 36 which is disposed in the insertion hole 30, and a biasing member (biasing means) 40, which biases the calibration member 36 toward an insertion port (tip opening) 38 of the insertion hole 30, are provided inside the casing 20 at the tip side thereof.

The insertion hole 30 extends in the longitudinal direction of the casing 20 and has a shape (quadrangular shape) corresponding to the shape of the base end side of the measuring chip 12 when viewed from the extending direction thereof. That is, when the measuring chip 12 is inserted in the insertion hole 30, the measuring chip 12 makes contact with a wall surface constituting the insertion hole 30. Thus, the measuring chip 12 is held at a predetermined measurement position by a frictional force (refer to FIGS. 5A and 5B). The blood glucose meter 10A may have a lock mechanism for holding the measuring chip 12 at a predetermined measurement position.

A disposing hole 44 communicates with the insertion hole 30. The disposing hole 44 is located at the base end side of the insertion hole 30 and extends along the longitudinal direction of the casing 20. An ejection pin (ejector) 42, which is connected to the ejection lever 22, is disposed in the disposing hole 44. That is, the ejection pin 42 is slidable in the extending direction of the insertion hole 30 by an operation of the ejection lever 22 by a user. The width dimension of the disposing hole 44 is smaller than the width dimension of the insertion hole 30. Accordingly, a bottom face 46 which is orientated to the insertion port 38 of the insertion hole 30 is formed at a boundary between the insertion hole 30 and the disposing hole 44.

The optical measurement unit 34 includes a light emitter 52, which is disposed in a first chamber 50 communicating with an introduction port 48, which is open on the wall surface constituting the insertion hole 30, a current feeder 54 (refer to FIG. 3), which feeds drive current to the light emitter 52, a light receiver 60 which is disposed in a second chamber 58 communicating with a lead-out port 56, which is open on the wall surface constituting the insertion hole 30, and an A/D converter 62 (refer to FIG. 3), which converts a light receiving signal of the light receiver 60 into a digital signal. The first chamber 50 and the second chamber 58 sandwich the insertion hole 30 from a direction perpendicular to the extending direction of the insertion hole 30, and the introduction port 48 and the lead-out port 56 face each other.

The light emitter 52 includes a first light emitting element 64 which applies light having a first wavelength to the measuring chip 12 and a second light emitting element 66 which applies light having a second wavelength different from the first wavelength to the measuring chip 12. The first light emitting element 64 and the second light emitting element 66 are mounted on a control board (not illustrated) and disposed, in the mounted state, at a position facing the introduction port 48.

In FIG. 2, the first light emitting element 64 and the second light emitting element 66 are arranged side by side in a direction perpendicular to the sheet. The first light emitting element 64 and the second light emitting element 66 may include, for example, light emitting diodes (LEDs). The first wavelength is a wavelength for detecting a coloration density of the reagent 18 corresponding to a blood glucose amount, for example, 620 to 640 nm. The second wavelength is a wavelength for detecting the concentration of red blood cells in blood, for example, 510 to 540 nm. The current feeder 54 feeds drive current to the first light emitting element 64 and the second light emitting element 66.

The light receiver 60 is mounted on a control board (not illustrated) and disposed, in the mounted state, at a position facing the lead-out port 56. The light receiver 60 receives transmitted light from the measuring chip 12 and may include a photodiode (PD).

The calibration member 36 is disposed in the insertion hole 30 slidably along the insertion direction of the measuring chip 12 (the extending direction of the insertion hole 30) and capable of blocking the introduction port 48 and the lead-out port 56. The calibration member 36 allows light emitted from the light emitter 52 (the first light emitting element 64 and the second light emitting element 66) to pass therethrough and also has a predetermined absorbance with respect to the light. In embodiments, the absorbance of the calibration member 36 with respect to the light is 1. The calibration member 36 having such a configuration can be made of, for example, an acrylic resin, a plastic such as polycarbonate, glass, or quartz so as to control optical characteristics to have a certain absorbance.

The biasing member 40 is interposed between the bottom face 46 which constitutes the insertion hole 30 and the calibration member 36. In other words, the biasing member 40 is fixed to the bottom face 46 and the calibration member 36 in an elastically deformable state along the extending direction of the insertion hole 30. An insertion path 68 through which the ejection pin 42 is inserted is formed in the biasing member 40. Although, in embodiments, the biasing member 40 is a compression coil spring which includes the insertion path 68 on the center thereof, the biasing member 40 may be, for example, a cylindrical body made of rubber. The compression coil spring enables the configuration of the biasing member 40 to be simplified.

Figure 5A:
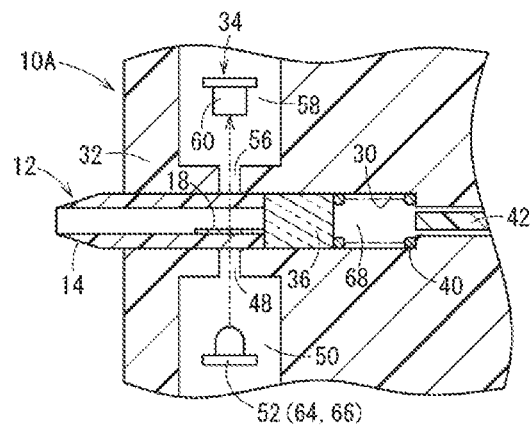
FIG. 5A is a partially-omitted sectional view illustrating a state in which the measuring chip of FIG. 1 is attached to the blood glucose meter.

In the blood glucose meter 10A configured in this manner, the calibration member 36 is held by the biasing member 40 at a position where the calibration member 36 blocks the introduction port 48 and the lead-out port 56 and where light from the light emitter 52 is applied to the calibration member 36 when the measuring chip 12 is not inserted in the insertion hole 30, and slides to the side opposite to the insertion port 38 along with the insertion of the measuring chip 12 into the insertion hole 30 so that light emitted from the light emitter 52 is applied to the measuring chip 12 (refer to FIG. 5A).

Figure 3:
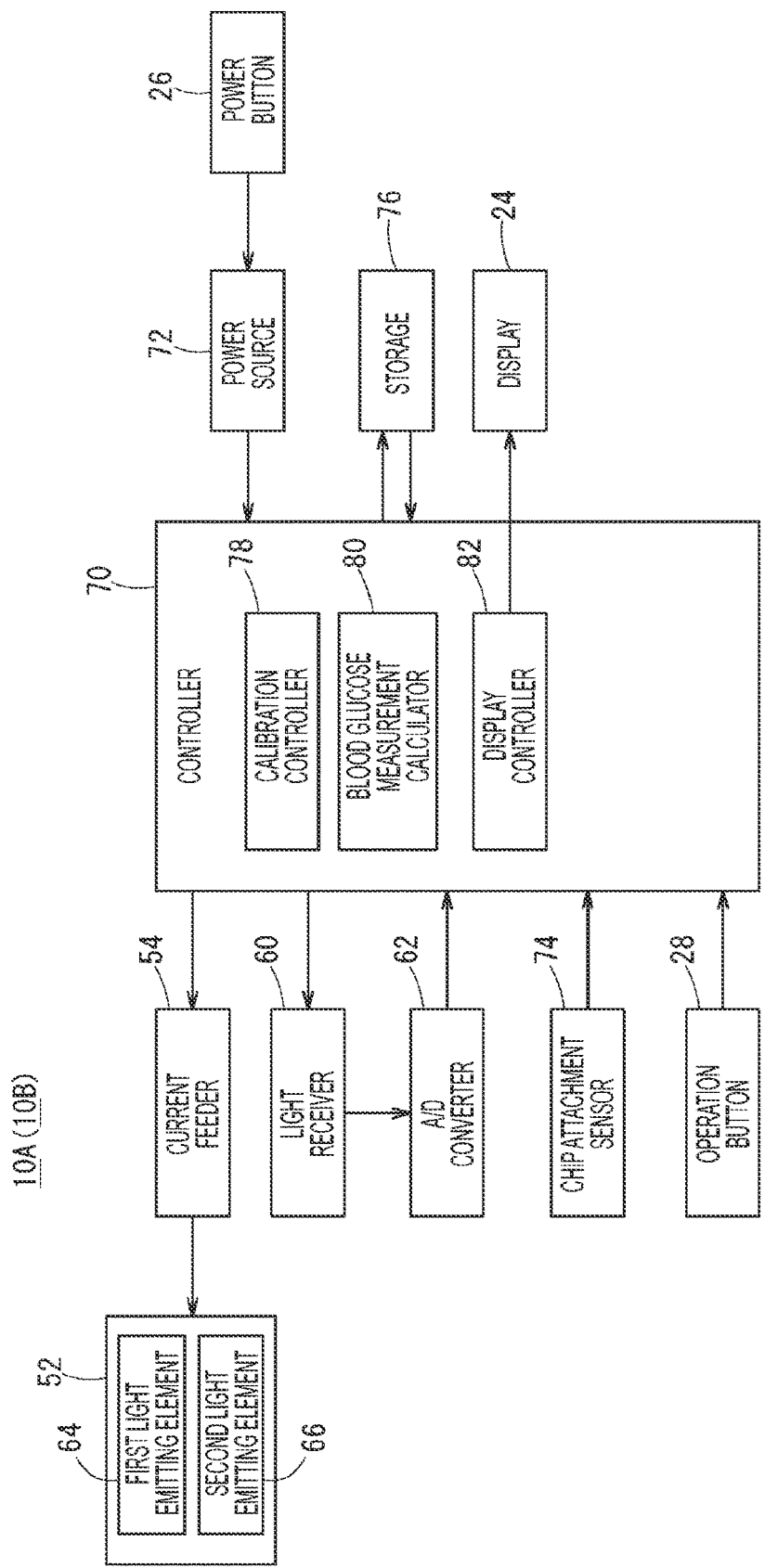
FIG. 3 is a block diagram describing a controller of the blood glucose meter of FIG. 1.

As illustrated in FIG. 3, the blood glucose meter 10A is further provided with a controller 70, the power source 72, a chip attachment sensor 74, and a storage 76. The controller 70 totally controls the entire blood glucose meter 10A. For example, a microcomputer is used as the controller 70 and reads a predetermined program to execute software processing in cooperation with each function unit. A detailed configuration of the controller 70 will be described below.

For example, a button battery is used as the power source 72 and supplies power to the controller 70 under the action of the power button 26. The chip attachment sensor 74 detects whether the measuring chip 12 has been attached to the insertion hole 30.

The storage 76 previously stores calibration curve data indicating the relationship between absorbance and blood glucose level, the absorbance and the blood glucose level of the calibration member 36, and the absorbance and the blood glucose level of an unused measuring chip 12. The storage 76 is capable of storing a blood glucose measured value which is actually measured.

The controller 70 includes a calibration controller 78, a blood glucose measurement calculator 80, and a display controller 82. The calibration controller 78 calibrates the blood glucose meter 10A for reducing a measurement error of the blood glucose level caused by aging of the light emitter 52 and the light receiver 60.

That is, the calibration controller 78 calibrates the blood glucose meter 10A on the basis of a first light receiving signal, which is output from the A/D converter 62, when the light receiver 60 receives transmitted light from the calibration member 36, and a second light receiving signal which is output from the A/D converter 62 when the light receiver 60 receives transmitted light from the measuring chip 12 before taking blood (an unreacted reagent 18).

Specifically, the calibration controller 78, for example, corrects and updates the calibration curve data (stores the corrected calibration curve data in the storage 76) on the basis of the first light receiving signal and the second light receiving signal to calibrate the blood glucose meter 10A.

The blood glucose measurement calculator 80 calculates the absorbance on the basis of a third light receiving signal which is output from the A/D converter 62 when the light receiver 60 receives transmitted light from the measuring chip 12 after taking blood (a colored reagent 18) and the second light receiving signal, and obtains a blood glucose measured value with reference to the updated calibration curve data stored in the storage 76.

The display controller 82 displays the blood glucose measured value calculated by the blood glucose measurement calculator 80 on the display 24.

The blood glucose meter 10A, according to embodiments, is basically configured as described above. Hereinbelow, the action and the effect of the blood glucose meter 10A will be described. In the blood glucose meter 10A in an initial state (when the measuring chip 12 is not inserted in the insertion hole 30), the calibration member 36 is located at the position where the calibration member 36 blocks the introduction port 48 and the lead-out port 56 and where light from the light emitter 52 is applied to the calibration member 36 (refer to FIG. 2). Accordingly, the intrusion of foreign substances into the first chamber 50 and the second chamber 58 from the outside is reduced. Thus, the contamination of the light emitter 52 and the light receiver 60 with foreign substances is reduced.

Figure 4:
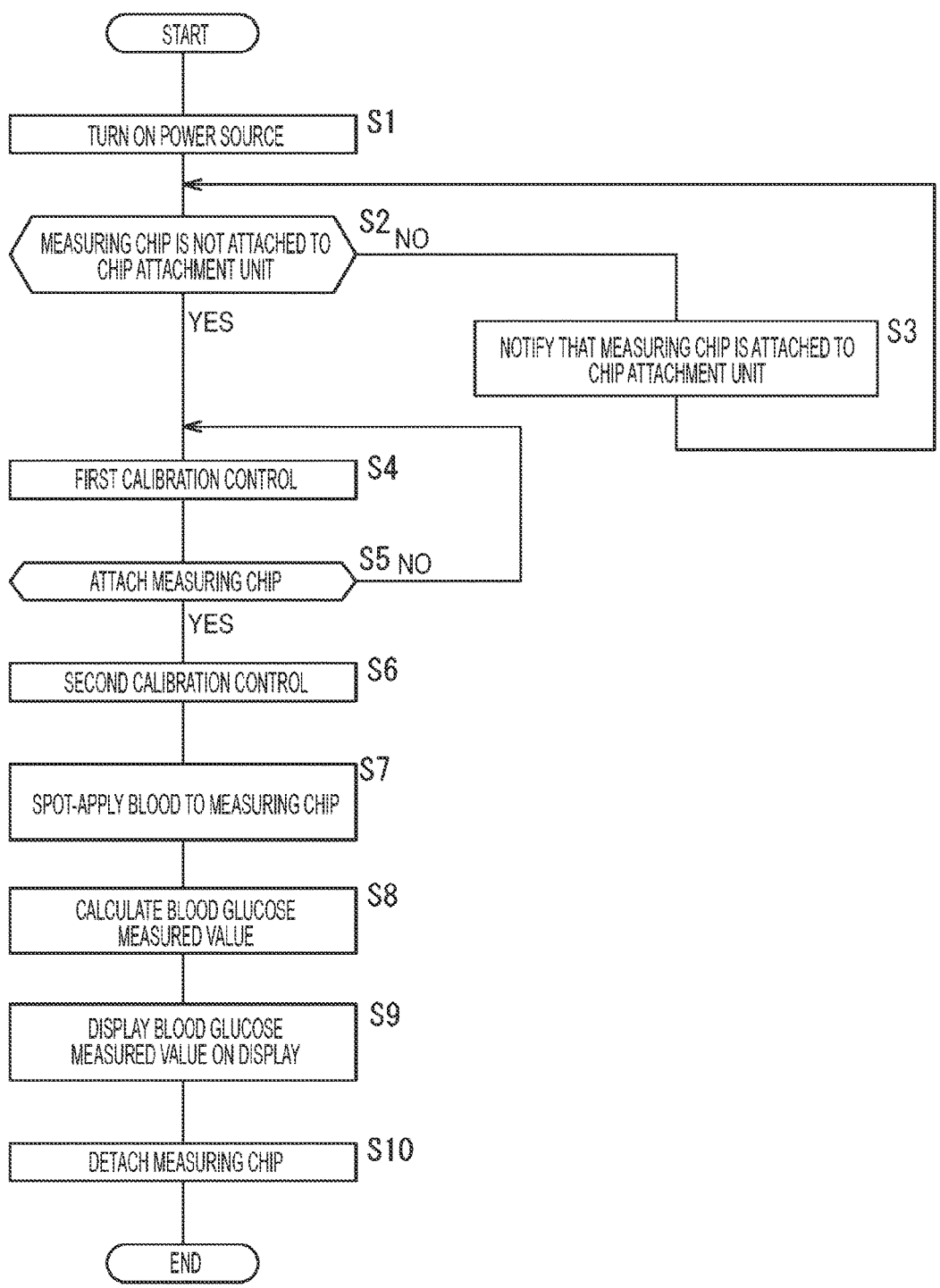
FIG. 4 is a flowchart describing a blood glucose measuring method using the blood glucose meter of FIG. 1.

When blood glucose measurement is performed using the blood glucose meter 10A, a user first presses the power button 26 to turn on the power source 72 of the blood glucose meter 10A (step S1 of FIG. 4). Accordingly, the controller 70 determines whether the measuring chip 12 is not attached to the chip attachment unit 32 on the basis of an output signal of the chip attachment sensor 74 (step S2).

When the controller 70 determines that the measuring chip 12 is attached to the chip attachment unit 32 (step S2: NO), the controller 70 notifies the determined result (the measuring chip 12 is attached to the chip attachment unit 32) to the user (step S3). Specifically, for example, the display controller 82 displays the determined result on the display 24. However, any method can be employed as the notification method of step S3, and, for example, the determination result may be notified to the user using sound.

On the other hand, when the controller 70 determines that the measuring chip 12 is not attached to the chip attachment unit 32 (step S2: YES), the controller 70 performs first calibration control (step S4). Specifically, the current feeder 54 alternately feeds current to the first light emitting element 64 and the second light emitting element 66.

Accordingly, the first light emitting element 64 and the second light emitting element 66 alternately apply light to the calibration member 36, the light receiver 60 receives transmitted light from the calibration member 36, and the A/D converter 62 outputs a first light receiving signal having a size corresponding to the intensity of the transmitted light to the controller 70. Then, the calibration controller 78 corrects the calibration curve data stored in the storage 76 on the basis of the first light receiving signal. Initial calibration curve data stored in the storage 76 is represented by a linear function of y=ax+c in an xy coordinate system of the absorbance and the blood glucose level (refer to a chain double-dashed line A of FIG. 6A).

Figure 6A:
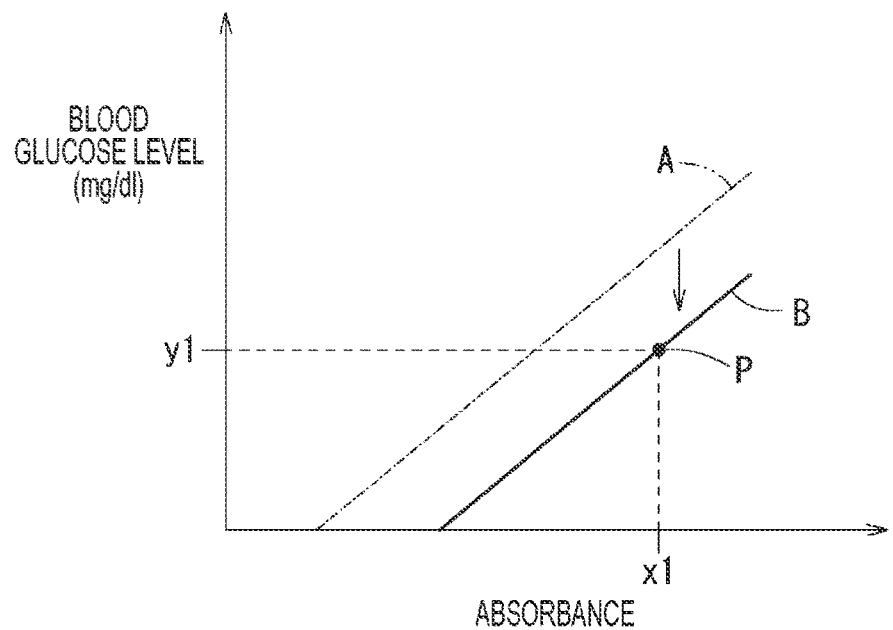
FIG. 6A is a graph for describing a first corrected calibration curve data.

Specifically, the calibration controller 78 calculates the absorbance of the calibration member 36 on the basis of the first light receiving signal, and corrects a constant term of the initial calibration curve data on the basis of the absorbance to obtain first corrected calibration curve data (y=ax+c1) (refer to a solid line B of FIG. 6A). In other words, the constant term of the initial calibration curve data is corrected so as to pass through a point P (x1, y1). Here, x1 denotes the calculated absorbance of the calibration member 36, and y1 denotes the blood glucose level of the calibration member 36 previously stored in the storage 76. The first corrected calibration curve data is stored in the storage 76.

Then, the user attaches the measuring chip 12 to the chip attachment unit 32. When the measuring chip 12 is inserted into the insertion hole 30, the calibration member 36 is pushed by the measuring chip 12 and thereby displaced toward the base end side while compressing the biasing member 40. Then, the base end side of the measuring chip 12 blocks the introduction port 48 and the lead-out port 56, and light from the light emitter 52 can be applied to the measuring chip 12 (refer to FIG. 5A). At this time, a frictional force is produced between the measuring chip 12 and the wall surface constituting the insertion hole 30. Thus, the position of the measuring chip 12 is not shifted by a restoring force of the biasing member 40.

The controller 70 determines whether the measuring chip 12 has been attached to the chip attachment unit 32 on the basis of an output signal of the chip attachment sensor 74 (step S5). When the controller 70 determines that the measuring chip 12 is not attached to the chip attachment unit 32 (step S5: NO), the processing on and after the above step S4 is performed.

On the other hand, when the controller 70 determines that the measuring chip 12 is attached to the chip attachment unit 32 (step S5: YES), the controller 70 performs second calibration control (step S6). Specifically, the current feeder 54 alternately feeds current to the first light emitting element 64 and the second light emitting element 66.

Accordingly, the first light emitting element 64 and the second light emitting element 66 alternately apply light to the measuring chip 12 before taking blood (an unreacted reagent 18), the light receiver 60 receives transmitted light from the measuring chip 12, and the A/D converter 62 outputs a second light receiving signal having a size corresponding to the intensity of the transmitted light to the controller 70. Then, the calibration controller 78 corrects the first corrected calibration curve data on the basis of the second light receiving signal.

Figure 6B:
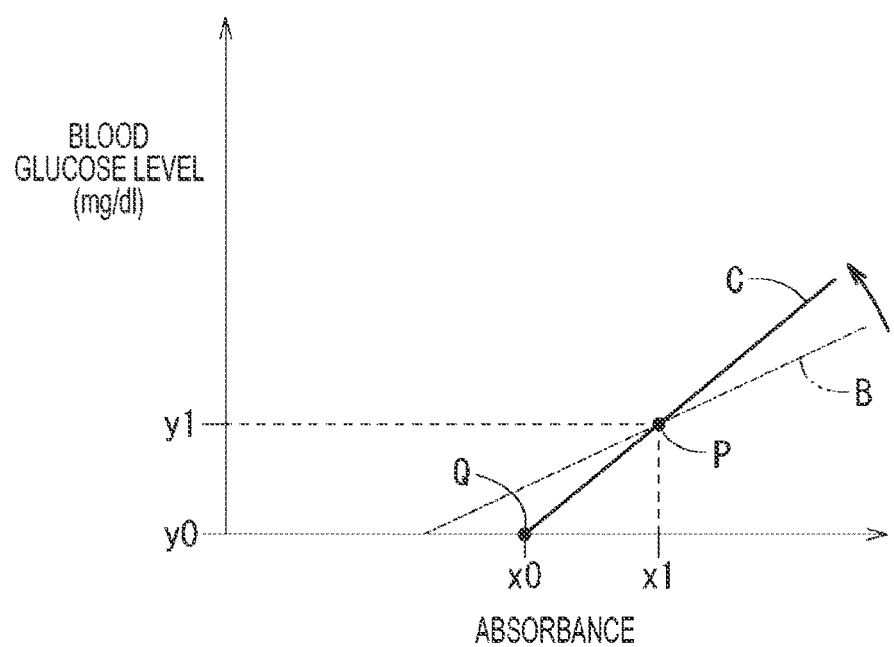
FIG. 6B is a graph for describing a second corrected calibration curve data.

Specifically, the calibration controller 78 calculates the absorbance of the measuring chip 12 before taking blood on the basis of the second light receiving signal, and corrects the gradient of the first corrected calibration curve data on the basis of the absorbance to obtain second corrected calibration curve data (y=a1x+c1) (refer to a solid line C of FIG. 6B). In other words, the gradient of the first corrected calibration curve data is corrected so as to pass through a point Q(x0, y0) in addition to the above point P(x1, y1).

Here, x0 denotes the calculated absorbance of the measuring chip 12, and y0 denotes the blood glucose level of the measuring chip 12 previously stored in the storage 76. The second corrected calibration curve data and the second light receiving signal are stored in the storage 76. Further, the first light emitting element 64 and the second light emitting element 66 continue the application of light to the measuring chip 12 also after the second calibration control.

Then, a part of the body of the user (e.g., a finger 84) is punctured with a puncture tool (not illustrated) to allow a small amount (e.g., approximately 0.3 to 1.5 µL) of blood to flow out on the skin. Then, the tip of the measuring chip 12 is spot-applied to the flowed-out blood (step S7). Accordingly, the blood is sucked into the blood introduction path 16 by a capillary phenomenon and reacts with the reagent 18, and the reagent 18 thereby shows a color corresponding to the blood glucose level.

Figure 5B:
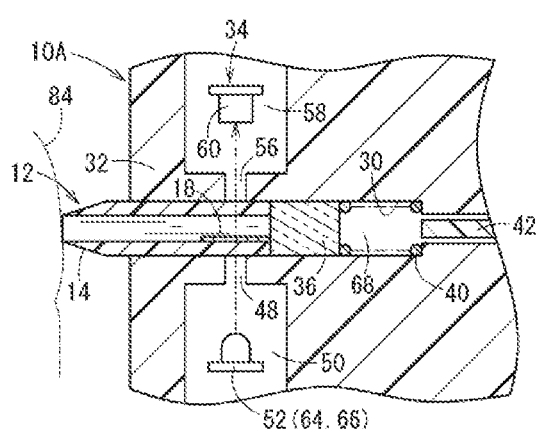
FIG. 5B is a partially-omitted sectional view illustrating a state in which blood is spot-applied to the measuring chip.

Then, as illustrated in FIG. 5B, light from the first light emitting element 64 and light from the second light emitting element 66 are alternately applied to the measuring chip 12 after taking the blood, the light receiver 60 receives transmitted light from the measuring chip 12 (the colored reagent 18), and the A/D converter 62 outputs a third light receiving signal having a size corresponding to the intensity of the transmitted light to the controller 70. Then, the blood glucose measurement calculator 80 calculates the absorbance from the second light receiving signal and the third light receiving signal.

Specifically, the absorbance relating to the first wavelength is calculated from the second light receiving signal of light emitted from the first light emitting element 64 and the third light receiving signal of light emitted from the first light emitting element 64, and the absorbance relating to the second wavelength is calculated from the second light receiving signal of light emitted from the second light emitting element 66 and the third light receiving signal of light emitted from the second light emitting element 66. The blood glucose measurement calculator 80 obtains a blood glucose measured value with reference to the absorbance relating to the first wavelength calculated from the second light receiving signal and the third light receiving signal and the second corrected calibration curve data, and further performs correction on a blood component on the basis of the absorbance relating to the second wavelength calculated from the second light receiving signal and the third light receiving signal to obtain a final blood glucose measured value (step S8).

Then, the display controller 82 displays the blood glucose measured value on the display 24 (step S9). Further, the user operates the ejection lever 22 to detach the used measuring chip 12 from the chip attachment unit 32 (step S10).

Figure 5C:
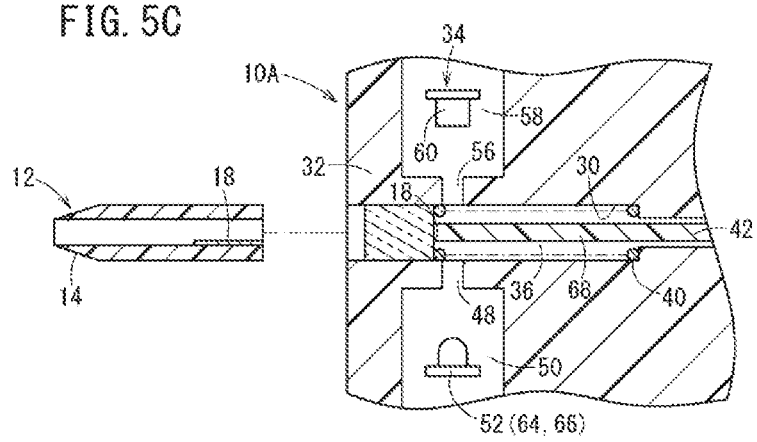
FIG. 5C is a partially-omitted sectional view illustrating a state in which the measuring chip is detached from the blood glucose meter.

Specifically, the ejection pin 42 displaces (slides) toward the insertion port 38 through the insertion path 68 of the biasing member 40 by the operation of the ejection lever 22, and the measuring chip 12 is pushed out by the ejection pin 42 through the calibration member 36 (refer to FIG. 5C). After the detachment of the measuring chip 12 from the insertion hole 30, the calibration member 36 displaced to the vicinity of the insertion port 38 returns to the position where the calibration member 36 blocks the introduction port 48 and the lead-out port 56 by the restoring force of the biasing member 40.

As described above, according to the blood glucose meter 10A, the introduction port 48 and the lead-out port 56 are blocked with the calibration member 36 in the initial state in which the measuring chip 12 is not inserted in the insertion hole 30. Thus, the intrusion of foreign substances into the introduction port 48 and the lead-out port 56 from the outside is reduced without providing a cover member for reducing the intrusion of foreign substances into the insertion hole 30. Thus, it is possible to improve the working efficiency (an attachment/detachment operation for the cover member is not required) and to reduce the contamination of the light emitter 52 and the light receiver 60 with foreign substances.

At this time, the calibration member 36 is held by the biasing member 40 at the position where light from the light emitter 52 (the first light emitting element 64 and the second light emitting element 66) is applied to the calibration member 36. Thus, when a user turns on the power source 72, the first corrected calibration curve data can be obtained on the basis of the first light receiving signal by the first calibration control. When the measuring chip 12 is inserted into the insertion hole 30, the calibration member 36 slides to the side opposite to the insertion port 38, and light from the light emitter 52 is applied to the measuring chip 12. Thus, it is possible to correct the first corrected calibration curve data on the basis of the second light receiving signal by the second calibration control to obtain the second corrected calibration curve data.

That is, the blood glucose meter 10A is calibrated at two points every time the blood glucose measurement is performed without calibrating the blood glucose meter 10A using a special calibration device. Thus, the blood glucose meter 10A can be appropriately calibrated. Further, the blood glucose level is obtained on the basis of the absorbance calculated from the second light receiving signal and the third light receiving signal and the second corrected calibration curve data by spot-applying blood to the measuring chip 12 inserted in the insertion hole 30. Thus, the measurement can be accurately performed.

In embodiments, a user operates the ejection lever 22 to displace the ejection pin 42 toward the insertion port 38 to slide the calibration member 36 toward the insertion port 38, which enables the measuring chip 12 to be easily and reliably detached from the insertion hole 30. According to such a configuration, it is possible to appropriately reduce the intrusion of foreign substances into the introduction port 48 and the lead-out port 56 from the outside through the insertion hole 30 when the measuring chip 12 is detached.

Further, the ejection pin 42 can be guided to the calibration member 36 through the insertion path 68 of the biasing member 40 which is disposed at the side opposite to the insertion hole 30 with respect to the calibration member 36 in the insertion hole 30. Thus, the blood glucose meter 10A can be downsized. Furthermore, since the biasing member 40 is a compression coil spring, the configuration of the biasing member 40 can be simplified.

Next, another blood glucose meter 10B as a component measuring device will be described. In the blood glucose meter 10B according to embodiments, the same components as those of the blood glucose meter 10A described above will be designated by the same reference signs, and detailed description thereof will be omitted.

Figure 7:
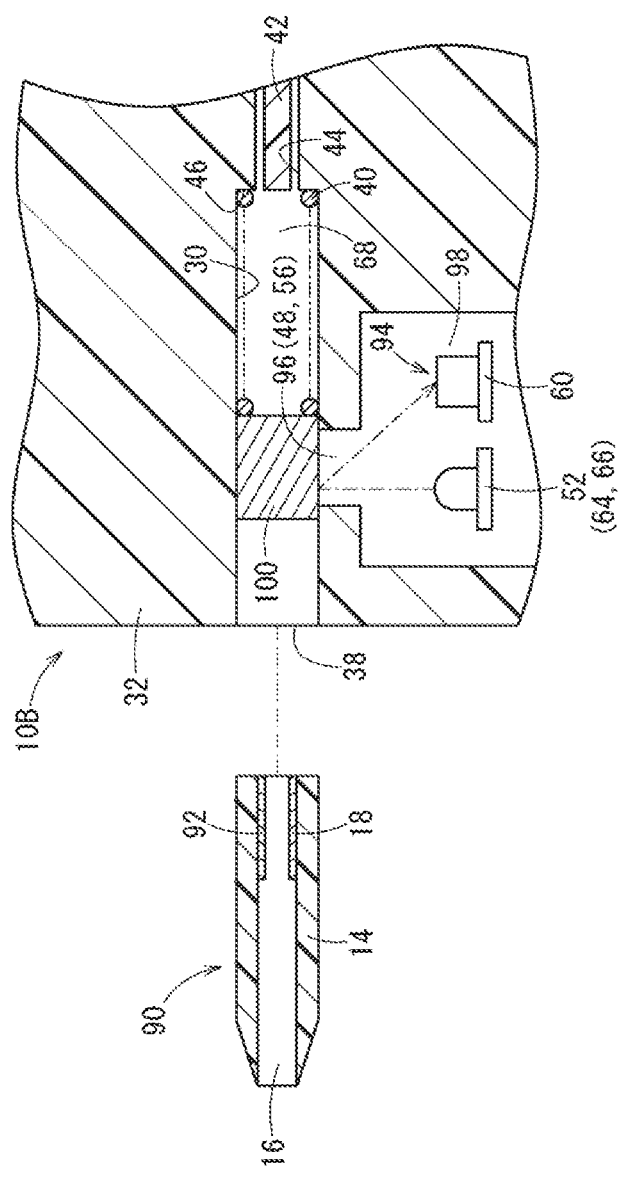
FIG. 7 is a longitudinal sectional view of an embodiment of a blood glucose meter and a measuring chip to be attached to the blood glucose meter.

As illustrated in FIG. 7, the blood glucose meter 10B is a colorimetric blood glucose meter which optically reflection-measures a blood glucose level in blood taken into a measuring chip 90.

First, the measuring chip 90 used in the blood glucose meter 10B will be described. The measuring chip 90 differs from the measuring chip 12 in that a reflector (reflective film) 92 which reflects light is formed in a region that faces the reagent 18 on the wall surface constituting the blood introduction path 16. The reflector 92 is a scatter reflection surface which is formed by depositing or applying a predetermined material to the region that faces the reagent 18 on the wall surface constituting the blood introduction path 16 by means such as vacuum deposition, sputtering, or plating. Examples of the predetermined material include metals such as aluminum, nickel and chromium, and white powders such as barium sulfate, titanium oxide and silicon dioxide.

In this case, when the chip body 14 is separable (e.g., equally separable) in the short-side direction, the formation of the reflector 92 and the application of the reagent 18 can be appropriately performed.

The blood glucose meter 10B, according to embodiments, includes an optical measurement unit 94 which differs from the optical measurement unit 34 of the blood glucose meter 10A in configuration. Specifically, in the optical measurement unit 94, the introduction port 48 and the lead-out port 56 are open on the wall surface constituting the insertion hole 30 and form one opening 96, and the light emitter 52 and the light receiver 60 are disposed in a chamber 98 which communicates with the opening 96. That is, the light emitter 52 (the first light emitting element 64 and the second light emitting element 66) and the light receiver 60 are mounted on a control board (not illustrated) and disposed, in the mounted state, at a position facing the opening 96.

A calibration member 100 reflects light emitted from the light emitter 52 and also has a predetermined absorbance with respect to the light. The calibration member 100 having such a configuration may include, for example, a reflective ND filter that includes a glass substrate coated with a chromium thin film or a plastic that includes one face mirror-finished with a metal thin film, appropriately contains a dye, a pigment or a filler, and has a known absorbance.

Figure 8A:
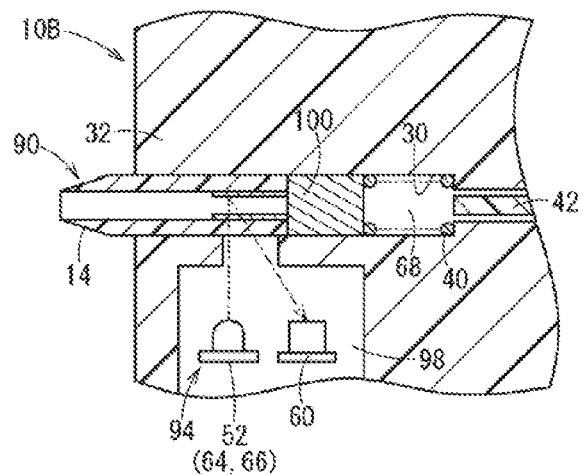
FIG. 8A is a partially-omitted sectional view illustrating a state in which the measuring chip of FIG. 7 is attached to the blood glucose meter.

In the blood glucose meter 10B configured in this manner, the calibration member 100 is held by the biasing member 40 at a position where the calibration member 100 blocks the opening 96 and where light from the light emitter 52 is applied to the calibration member 100 when the measuring chip 90 is not inserted in the insertion hole 30, and slides to the side opposite to the insertion port 38 along with the insertion of the measuring chip 90 into the insertion hole 30 so that light emitted from the light emitter 52 is applied to the measuring chip 90 (refer to FIG. 8A).

The blood glucose meter 10B having such a configuration basically performs blood glucose measurement in accordance with the flow chart of FIG. 4. Here, changed points in step S4, step S6, and step S8 will be briefly described.

In embodiments, as illustrated in FIG. 7, the light receiver 60 receives reflected light from the calibration member 100, and the A/D converter 62 outputs a first light receiving signal having a size corresponding to the intensity of the reflected light to the controller 70 in first calibration control (step S4). Then, the calibration controller 78 performs processing similar to step S4 of the above first embodiment to correct initial calibration curve data to obtain first corrected calibration curve data.

As illustrated in FIG. 8A, reflected light from the measuring chip 90 before taking blood is received, and the A/D converter 62 outputs a second light receiving signal having a size corresponding to the intensity of the reflected light to the controller 70 in second calibration control (step S6). Then, the calibration controller 78 performs processing of the second calibration control of the above first embodiment to correct the first corrected calibration curve data to obtain second corrected calibration curve data.

Figure 8B:
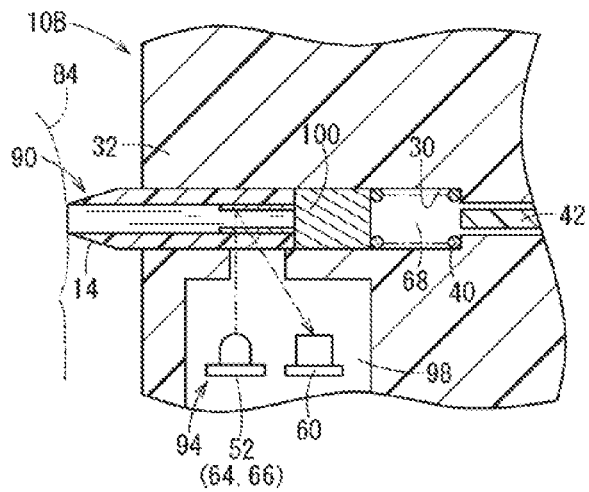
FIG. 8B is a partially-omitted sectional view illustrating a state in which blood is spot-applied to the measuring chip.

As illustrated in FIG. 8B, in the calculation of a blood glucose measured value (step S8), the light receiver 60 receives reflected light from the measuring chip 90 after taking blood, and the A/D converter 62 outputs a third light receiving signal having a size corresponding to the intensity of the reflected light to the controller 70. Then, a blood glucose measurement calculator 80 obtains a blood glucose measured value with reference to the absorbance relating to the first wavelength calculated from the second light receiving signal and the third light receiving signal and the second corrected calibration curve data, and further performs correction on a blood component on the basis of the absorbance relating to the second wavelength calculated from the second light receiving signal and the third light receiving signal to obtain a final blood glucose measured value.

As described above, the blood glucose meter 10B achieves an effect similar to the effect of the blood glucose meter 10A describe above.

The blood glucose meters 10A, 10B and the blood glucose measuring methods using the blood glucose meters 10A, 10B are not limited to the above examples. For example, a first light receiving signal having a size corresponding to light from the calibration member 36, 100 may be stored in the storage 76 in step S4, and in step S6, initial calibration curve data may be corrected on the basis of a second light receiving signal having a size corresponding to light from the measuring chip 12, 90 before taking blood and the first light receiving signal stored in the storage 76 to obtain corrected calibration curve data. Also in this case, the initial calibration curve data can be calibrated at two points, and the blood glucose meter 10A, 10B can thus be appropriately calibrated.

The calibration controller 78 may correct at least either the light emitter 52 or the light receiver 60 on the basis of the first light receiving signal and the second light receiving signal to calibrate the blood glucose meter 10A, 10B without correcting the calibration curve data.

In this case, in the first calibration control in step S4, the calibration controller 78 calculates the absorbance of the calibration member 36, 100 on the basis of the first light receiving signal. Then, at least either the light emitter 52 or the light receiver 60 is corrected so that the calculated absorbance coincides with the absorbance of the calibration member 36, 100 stored in the storage 76.

When the light emitter 52 is corrected, the calibration controller 78 controls the current feeder 54 to adjust values of drive current fed to the first light emitting element 64 and the second light emitting element 66. Specifically, the calibration controller 78 adjusts a value of drive current fed to the first light emitting element 64 on the basis of the absorbance relating to the first wavelength calculated from the first light receiving signal and adjusts a value of drive current fed to the second light emitting element 66 on the basis of the absorbance relating to the second wavelength calculated from the first light receiving signal. On the other hand, when the light receiver 60 is corrected, the calibration controller 78 adjusts the sensitivity of the light receiver 60.

Then, in the second calibration control in step S6, the controller 70 calculates the absorbance of the calibration member 36, 100 on the basis of the second light receiving signal. Then, similarly to the first calibration control, at least either the light emitter 52 or the light receiver 60 is corrected so that the calculated absorbance coincides with the absorbance of the calibration member 36 stored in the storage 76.

In this manner, even when the blood glucose meter 10A, 10B is calibrated by correcting at least either the light emitter 52 or the light receiver 60, the blood glucose meter 10A, 10B can be appropriately calibrated by performing two-point calibration (two-time calibration) using the calibration member 36 and the measuring chip 12 before taking blood.

In the blood glucose measuring method using the blood glucose meter 10A, 10B, the first calibration control of step S4 may be performed and the second calibration control of step S6 may be omitted. This approach enables the control of the blood glucose meter 10A, 10B to be simplified. Also in this case, the controller 70 requires detecting the second light receiving signal (background correction data) used in the calculation of a blood glucose measured value in step S6.

It is needless to say that the component measuring device is not limited to the above embodiments and can employ various configurations without departing from the gist of the invention. Although, in each of the above embodiments, the blood glucose meter that measures a blood glucose level in blood has been described, the component measuring device may be any device that measures a predetermined component in a body fluid (e.g., urine) other than blood.

The invention claimed is:

1. A component measuring device that measures a predetermined component in a body fluid taken into a measuring chip, the component measuring device comprising:
   a chip attachment unit including an insertion hole into which the measuring chip is inserted via an insertion port of the insertion hole;
   a light emitter disposed on a first side of the insertion hole that applies light to the measuring chip from the first side of the insertion hole and through an introduction port open on the first side of the insertion hole;
   a light receiver disposed on a second side of the insertion hole that receives light from the measuring chip guided through a lead-out port open on the second side of the insertion hole, wherein the second side of the insertion hole is disposed opposite the first side of the insertion hole;
   a calibration member slidably disposed in the insertion hole along an insertion direction of the measuring chip, the calibration member having an initial state and a mounted state, wherein the calibration member is disposed in a first position between the light emitter and the light receiver blocking the introduction port and the lead-out port in the initial state, and wherein the calibration member is slidably displaced along the insertion direction opposite the insertion port from the first position to a second position clear of the introduction port and the lead-out port such that light from the light emitter is applied to the measuring chip in the mounted state; and
   a calibration controller that calibrates calibration curve data based on a light receiving signal of the light receiver receiving light from the calibration member in the initial state, and a light receiving signal of the light receiver receiving light from the measuring chip before taking the body fluid in the mounted state and calculates an absorbance based on the light receiving signal of the light receiver receiving light from the measuring chip before taking the body fluid in the mounted state and a light receiving signal of the light receiver receiving light from the measuring chip after taking the body fluid in the mounted state and obtains a value of the predetermined component with reference to the absorbance and the calibration curve data.

2. The component measuring device according to claim 1, further comprising:
   a biasing member that biases the calibration member toward the insertion port of the insertion hole; and
   an ejector that slides the calibration member toward the insertion port to detach the measuring chip from the insertion hole.

3. The component measuring device according to claim 2, wherein the biasing member is disposed at a side opposite to the insertion port with respect to the calibration member in the insertion hole and includes an insertion path through which the ejector is inserted.

4. The component measuring device according to claim 3, wherein the biasing member is a compression coil spring including the insertion path on the center thereof.

5. The component measuring device according to claim 1, wherein
   the introduction port and the lead-out port face each other, and
   the light receiver receives transmitted light from the calibration member in the initial state, and
   the light receiver receives transmitted light from the measuring chip in the mounted state.

6. A method for measuring a predetermined component in a body fluid taken into a measuring chip, the method comprising:
   providing a chip attachment unit including an insertion hole into which the measuring chip is inserted via an insertion port of the insertion hole;
   applying, by a light emitter disposed on a first side of the insertion hole, light to the measuring chip from the first side of the insertion hole and through an introduction port open on the first side of the insertion hole;
   receiving, by a light receiver disposed on a second side of the insertion hole, light from the measuring chip guided through a lead-out port open on the second side of the insertion hole, wherein the second side of the insertion hole is disposed opposite the first side of the insertion hole;
   calibrating, by a controller, calibration curve data based on a light receiving signal of the light receiver receiving light from a calibration member in an initial state, and a light receiving signal of the light receiver receiving light from the measuring chip before taking the body fluid in a mounted state, wherein the calibration member is disposed in a first position between the light emitter and the light receiver blocking the introduction port and the lead-out port in the initial state, and wherein the calibration member is slidably displaced along an insertion direction opposite the insertion port from the first position to a second position clear of the introduction port and the lead-out port such that light from the light emitter is applied to the measuring chip in the mounted state;
   calculating, by the controller, an absorbance based on the light receiving signal of the light receiver receiving light from the measuring chip before taking the body fluid in the mounted state and a light receiving signal of the light receiver receiving light from the measuring chip after taking the body fluid in the mounted state; and obtaining, by the controller, a value of the predetermined component with reference to the absorbance and the calibration curve data.

7. The method according to claim 6, further comprising:
biasing, by a biasing member, the calibration member toward the insertion port of the insertion hole; and
sliding, by an ejector, the calibration member in a direction toward the insertion port detaching the measuring chip from the insertion hole.

8. The method according to claim 7, wherein the biasing member is disposed at a side opposite to the insertion port with respect to the calibration member in the insertion hole and includes an insertion path through which the ejector is inserted.

9. The method according to claim 8, wherein the biasing member is a compression coil spring including the insertion path on the center thereof.

10. The method according to claim 6, wherein
the introduction port and the lead-out port face each other, and wherein the method further comprises:
receiving, by the light receiver, transmitted light from the calibration member in the initial state; and
receiving, by the light receiver, transmitted light from the measuring chip in the mounted state.

11. A component measuring device that measures a predetermined component in a body fluid taken into a measuring chip, the component measuring device comprising:
a chip attachment unit comprising:
an insertion hole that receives a measuring chip inserted into an insertion port of the insertion hole;
a first chamber disposed on a first side of the insertion hole;
a second chamber disposed on a second side of the insertion hole opposite the first side of the insertion hole;
an opening running from the first chamber through the insertion hole to the second chamber; and
a calibration member slidably disposed in the insertion hole along an insertion direction of the measuring chip, the calibration member having an initial state and a mounted state, wherein the calibration member is disposed in a first position between the first chamber and the second chamber blocking the opening in the initial state, and wherein the calibration member is slidably displaced along the insertion direction opposite the insertion port from the first position to a second position clear of the opening such that light from the light emitter is applied to the measuring chip inserted into the insertion port of the insertion hole in the mounted state;
a light emitter disposed in the first chamber that emits light through a first portion of the opening adjacent to the first side of the insertion hole;
a light receiver disposed in the second chamber that receives light from a second portion of the opening adjacent to the second side of the insertion hole; and
a controller that calibrates calibration curve data based on a light signal received by the light receiver from the calibration member in the initial state and a light signal received by the light receiver from the measuring chip in the mounted state and before taking the body fluid into the measuring chip, calculates
an absorbance based on the light signal received by the light receiver from the measuring chip in the mounted state and before taking the body fluid into the measuring chip and a light signal received by the light receiver from the measuring chip in the mounted state and after taking the body fluid into the measuring chip, and
obtains a value of the predetermined component with reference to the absorbance and the calibration curve data.

12. The component measuring device according to claim 11, further comprising:
a biasing member that biases the calibration member toward the insertion port of the insertion hole; and
an ejector that slides the calibration member toward the insertion port to detach the measuring chip from the insertion hole.

13. The component measuring device according to claim 12, wherein the biasing member is disposed inside the insertion hole at a side of the insertion hole opposite the insertion port and includes an insertion path disposed in a center of the biasing member through which the ejector slides.

14. The component measuring device according to claim 13, wherein the biasing member is a compression coil spring including a first end that remains in contact with the calibration member in the initial state and in the mounted state.

15. The component measuring device according to claim 11, wherein
the introduction port and the lead-out port face each other,
the light receiver receives transmitted light from the calibration member in the initial state; and
the light receiver receives transmitted light from the measuring chip in the mounted state.

16. The component measuring device according to claim 11, wherein the calibration member blocks foreign contaminants from entering the opening and contaminating the light emitter and the light receiver in the initial state.

17. The component measuring device according to claim 11, wherein the first portion of the opening and the second portion of the opening are aligned along an axis that is disposed substantially perpendicular to an axis of the insertion hole.

18. The component measuring device according to claim 11, wherein the calibration member is completely disposed within the insertion hole in the initial state and in the mounted state.

* * * * *